(12) United States Patent
Kimelman

(10) Patent No.: US 6,177,051 B1
(45) Date of Patent: Jan. 23, 2001

(54) DISPENSABLE ALCOHOL BREATH ANALYZER SYSTEM

(76) Inventor: Rosemarie L. Kimelman, 12990 Southwest 56th St., Fort Lauderdale, FL (US) 33330-3230

( * ) Notice: Under 35 U.S.C. 154(b), the term of this patent shall be extended for 0 days.

(21) Appl. No.: 09/121,334

(22) Filed: Jul. 23, 1998

(51) Int. Cl.[7] .................................................. G01N 33/48
(52) U.S. Cl. ................. 422/85; 422/84; 422/58; 422/61; 436/132; 436/900; 73/23.3
(58) Field of Search ................. 422/83–85, 58, 422/61; 436/132, 900; 73/23.3

(56) References Cited

U.S. PATENT DOCUMENTS

| 3,877,291 | * | 4/1975 | Hoppesch et al. ............. 73/23.3 |
| 5,303,575 | * | 4/1994 | Brown et al. ................. 422/84 |
| 5,834,626 | * | 11/1998 | De Castro et al. ............. 73/23.3 |

* cited by examiner

Primary Examiner—Lyle A. Alexander

(57) ABSTRACT

A dispensable alcohol breath analyzer system including a rectilinear box with an analyzer on one face and an extendable tube on another face. The system also includes a plurality of units located within the box to be dispensed, each unit containing an analyzer and a sanitary wrapper therearound. The indicator includes a cylindrical alcohol indicator and an associated rotatable indicator arrow. A gauge is provided whereby the increased content of alcohol permeates through the indicator to rotate the arrow to an extent corresponding to the percent of alcohol within the breath detected. The second indicator includes a diaphragm through which the user's breath may flow to exterior of the device and an associated color gauge thereadjacent whereby the diaphragm will change colors as a function of the percent of alcohol in the breath of the user for being compared with the color on the gauge.

1 Claim, 3 Drawing Sheets

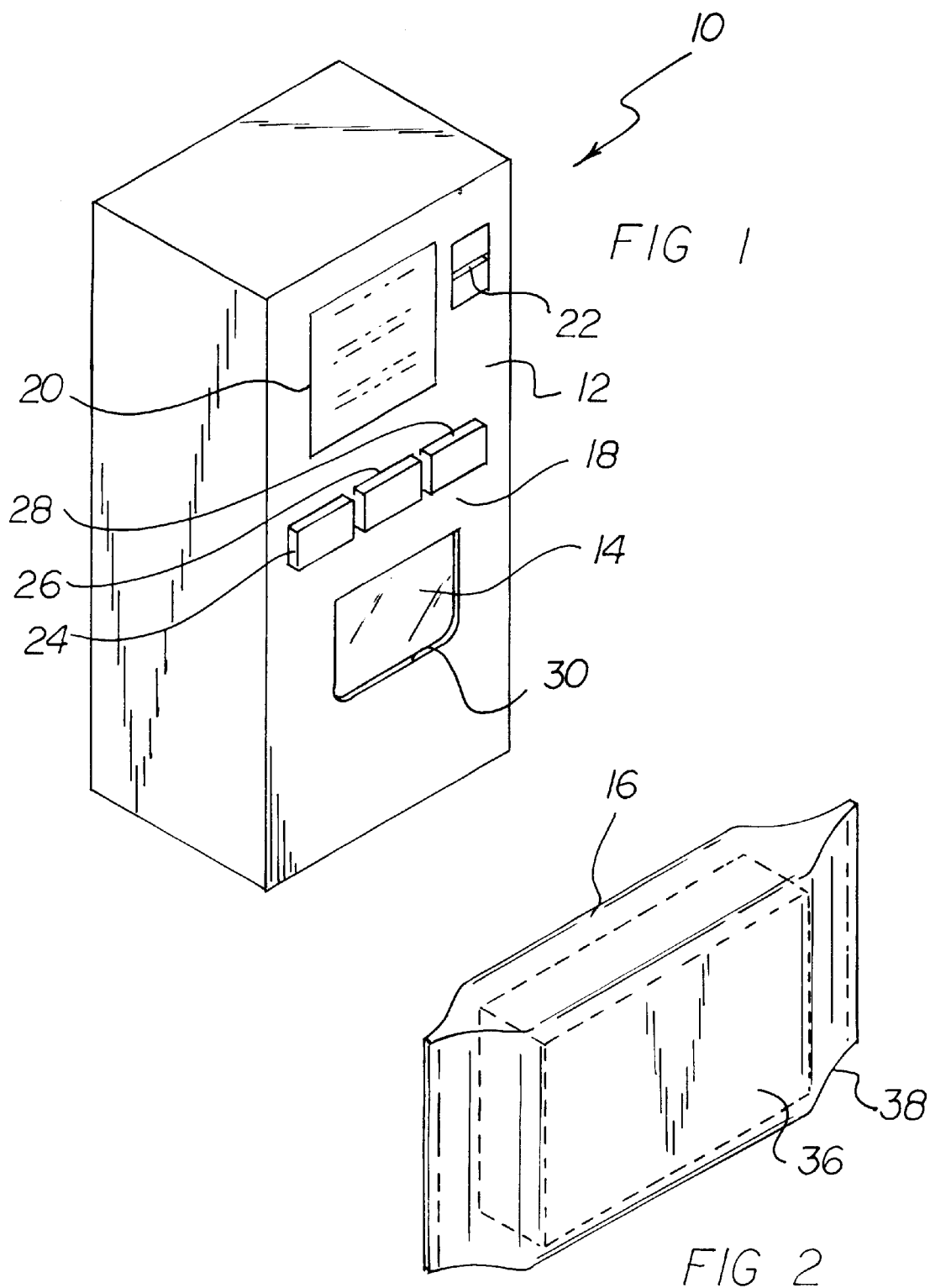

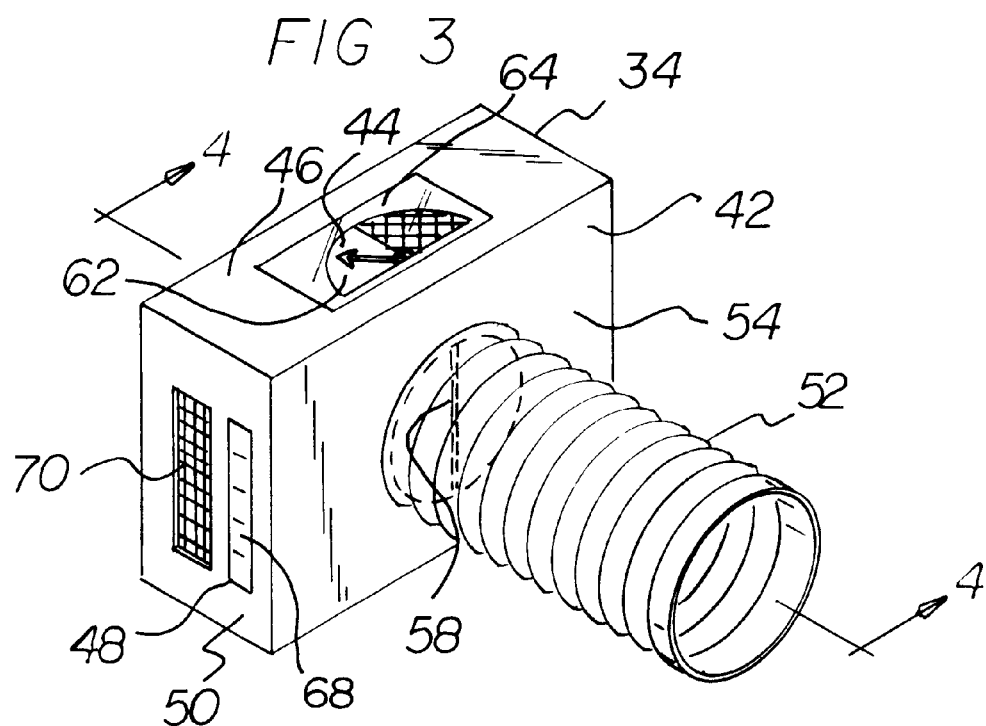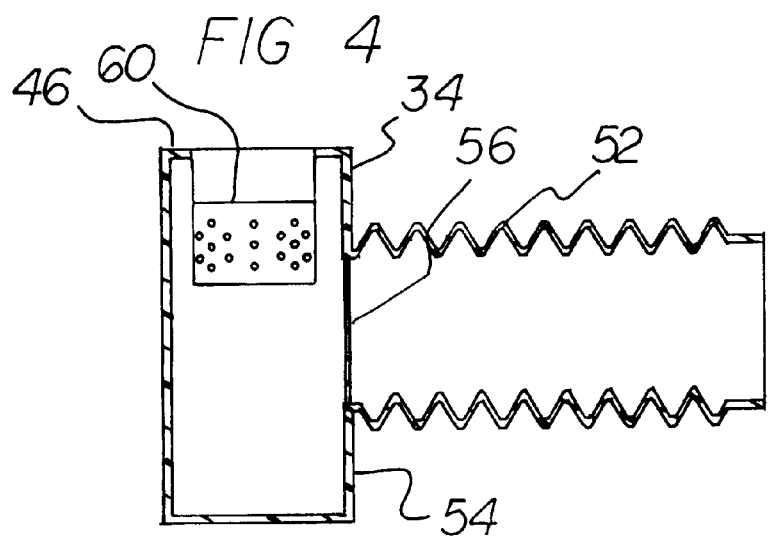

DISPENSABLE ALCOHOL BREATH ANALYZER SYSTEM

BACKGROUND OF THE INVENTION

1. Field of the Invention

The present invention relates to a dispensable alcohol breath analyzer system and more particularly pertains to self-analyzing one's breath for alcohol content.

2. Description of the Prior Art

The use of breath analyzers of known designs and configurations is known in the prior art. More specifically, breath analyzers of known designs and configurations heretofore devised and utilized for the purpose of analyzing a person's breath by known methods and apparatuses are known to consist basically of familiar, expected, and obvious structural configurations, notwithstanding the myriad of designs encompassed by the crowded prior art which has been developed for the fulfillment of countless objectives and requirements.

By way of example, U.S. Pat. No. 5,171,535 to Lamont discloses a Breath Alcohol Tester. U.S. Pat. No. 4,492,673 to Eriksen et al. discloses a Disposable Sobriety Tester. U.S. Pat. No. 5,415,391 to Risolia discloses a Vending Machine. U.S. Pat. No. 2,141,646 to C. Ferguson discloses a Device for Detecting Ethyl Alcohol. International Application Number PCT/US84/00345 to Schmitz discloses a Disposable Breath Analyzer Device and Method of Fabrication. Lastly, U.S. Pat. No. 3,437,448 to Miczka discloses an Apparatus for Determining the Alcohol Content of Exhaled Air.

In this respect, the a dispensable alcohol breath analyzer system according to the present invention substantially departs from the conventional concepts and designs of the prior art, and in doing so provides an apparatus primarily developed for the purpose of self-analyzing one's breath for alcohol content.

Therefore, it can be appreciated that there exists a continuing need for a new and improved a dispensable alcohol breath analyzer system which can be used for self-analyzing one's breath for alcohol content. In this regard, the present invention substantially fulfills this need.

SUMMARY OF THE INVENTION

In view of the foregoing disadvantages inherent in the known types of breath analyzers of known designs and configurations now present in the prior art, the present invention provides an improved a dispensable alcohol breath analyzer system. As such, the general purpose of the present invention, which will be described subsequently in greater detail, is to provide a new and improved a dispensable alcohol breath analyzer system and method which has all the advantages of the prior art and none of the disadvantages.

To attain this, the present invention essentially comprises a new and improved a dispensable alcohol breath analyzer system for self-analyzing one's breath for alcohol content. The system includes a dispenser machine which has an interior chamber containing units to be dispensed and a front face. The front face has a panel of instructions, a slot for the receipt of money and three buttons adapted to be depressed by a user following the insertion of money into the slot to indicate whether one or two or three units are to be dispensed. The machine also has an opening in the lower extent of the machine through which a user may reach to withdraw units from the machine following the insertion of money and depression of a button. A plurality of units are located within the chamber to be dispensed. Each unit contains an analyzer and a sanitary wrapper therearound. Each analyzer is formed as a generally rectilinear box with a first indicator on one face, a second indicator on a second face and an extendable tube on a third face. The extendible tube is reconfigurable between a reduced orientation adjacent to the third face when wrapped within the wrapper and an extended orientation for being gripped by the mouth of the user during the analyzing of the user's breath and with a slot in the third face adjacent to the tube. The first indicator includes a cylindrical alcohol indicator and an associated rotatable indicator arrow and a gauge whereby the increased content of alcohol permeating through the indicator will rotate the arrow to an extent corresponding to the percent of alcohol within the breath detected. The second indicator includes a diaphragm through which the user's breath may flow to exterior of the device and an associated color gauge there adjacent whereby the diaphragm will change colors as a function of the percent of alcohol in the breath of the user for being compared with the color on the gauge.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved a dispensable alcohol breath analyzer system which has all of the advantages of the prior art breath analyzers of known designs and configurations and none of the disadvantages.

It is another object of the present invention to provide a new and improved a dispensable alcohol breath analyzer system which may be easily and efficiently manufactured and marketed.

It is further object of the present invention to provide a new and improved a dispensable alcohol breath analyzer system which is of durable and reliable constructions and formed of recyclable materials.

An even further object of the present invention is to provide a new and improved a dispensable alcohol breath analyzer system which is susceptible of a low cost of manufacture with regard to both materials and labor, and which accordingly is then susceptible of low prices of sale to the consuming public, thereby making such a dispensable alcohol breath analyzer system economically available to the buying public.

Even still another object of the present invention is to provide a dispensable alcohol breath analyzer system for self-analyzing one's breath for alcohol content.

Lastly, it is an object of the present invention to provide a new and improved dispensable alcohol breath analyzer system including a rectilinear box with an analyzer on one face and an extendable tube on another face. The system also includes a plurality of units located within the box to be dispensed, each unit containing an analyzer and a sanitary wrapper therearound. The indicator includes a cylindrical alcohol indicator and an associated rotatable indicator arrow. A gauge is provided whereby the increased content of alcohol permeates through the indicator to rotate the arrow to an extent corresponding to the percent of alcohol within the breath detected. The second indicator includes a diaphragm through which the user's breath may flow to exterior of the device and an associated color gauge there adjacent whereby the diaphragm will change colors as a function of the percent of alcohol in the breath of the user for being compared with the color on the gauge.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a perspective view of the dispensable alcohol breath analyzer system constructed in accordance with the primary embodiment of the present invention.

FIG. 2 is a unit adapted to be dispensed from the machine of the system shown in FIG. 1.

FIG. 3 is a breath analyzer contained within the unit of FIG. 2.

FIG. 4 is a cross-sectional view taken along line 4—4 of FIG. 3.

The same reference numerals refer to the same parts through the various Figures.

DESCRIPTION OF THE PREFERRED EMBODIMENT

Figure 5:
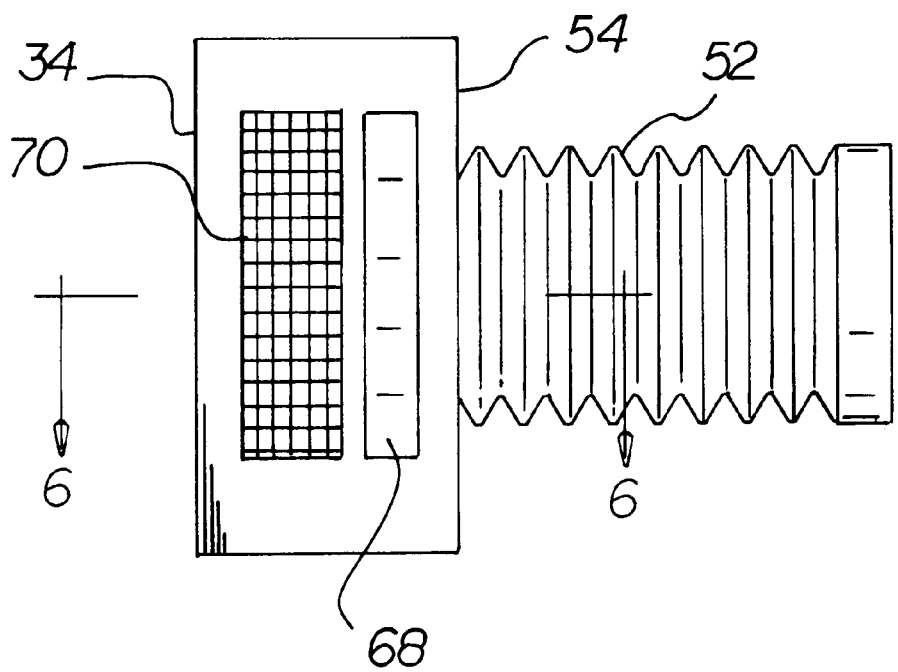
FIG. 5 is a side elevational view of the analyzer shown in FIG. 3.
Figure 6:
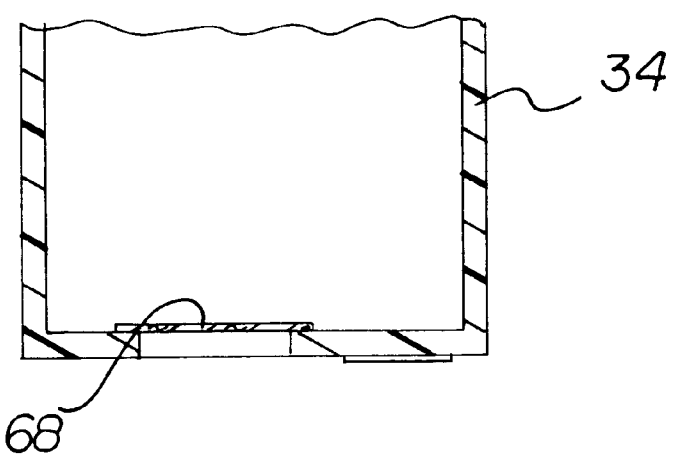
FIG. 6 is a cross-sectional view taken along line 6—6 of FIG. 5.

With reference now to the drawings, and in particular to FIG. 1 thereof, the preferred embodiment of the new and improved a dispensable alcohol breath analyzer system embodying the principles and concepts of the present invention and generally designated by the reference numeral 10 will be described.

The present invention, the a dispensable alcohol breath analyzer system 10 is comprised of a plurality of components. Such components are individually configured and correlated with respect to each other so as to attain the desired objective.

More specifically, the new and improved dispensable alcohol breath analyzer system 10 for self-analyzing one's breath for alcohol content comprises a dispenser machine 12 having an interior chamber 14 containing units 16 to be dispensed and a front face 18. The front face has a panel 20 of instructions, a slot 22 for the receipt of money and three buttons 24, 26, 28 adapted to be depressed by a user following the insertion of money into the slot to indicate whether one or two or three units are to be dispensed. The front face also has an opening 30 in the lower extent of the machine through which a user may reach to withdraw units from the machine following the insertion of money and depression of a button.

Also provided is a plurality of units 34 located within the chamber to be dispensed. Each unit contains an analyzer 36 and a sanitary wrapper 38 therearound.

Each analyzer is formed as a generally rectilinear box 42 with a first indicator 44 on one face 46, a second indicator 48 on a second face 50 and an extendable tube 52 on a third face 54. The extendible tube is reconfigurable between a reduced orientation adjacent to the third face when wrapped within the wrapper and an extended orientation for being gripped by the mouth of the user during the analyzing of the user's breath and with a slot 56 in the third face adjacent to the tube.

The first indicator includes a cylindrical alcohol indicator 60 and an associated rotatable indicator arrow 62 and a gauge 64 whereby the increased content of alcohol permeating through the indicator will rotate the arrow to an extent corresponding to the percent of alcohol within the breath detected.

The second indicator includes a diaphragm 68 through which the user's breath may flow to exterior of the device and an associated color gauge 70 there adjacent whereby the diaphragm will change colors as a function of the percent of alcohol in the breath of the user for being compared with the color on the gauge.

As described hereinabove, the present invention is a device designed to test the blood/alcohol concentration (BAC) of a person prior to driving. It assists the individual in determining if he or she is in safe and legal condition to drive a motor vehicle after having consumed alcohol.

The invention could easily be dispensed from vending machines in locations where potential drivers may question their level of intoxication. The device measures approximately 2½ to 3 inches tall, 6 to 8 inches long, and 2 to 2½ inches wide. The front face contains a collapsible mouthpiece through which the purchaser breathes to have the BAC tested. A slit or perforated/porous membrane is included at the end of the tubular mouthpiece where it contacts the rectangular base. This requires the user to build up air pressure within the mouthpiece to puncture the seal for an accurate reading.

A color-coded paper is incorporated into the design for analyzing the user's breath and turns a color according to the level of intoxication. Another alternative is the use of a small meter reading that displays the user's BAC. Either display means is easily readable when viewed at the top or side of the device.

The appealing features of the present invention are its convenience, ease of use, and anticipated decrease in the number of driving accidents related to alcohol. The device could be used by a person in a discrete and private manner.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A dispensable alcohol breath analyzer system for self-analyzing one's breath for alcohol content comprising, in combination:

a dispenser machine having an interior chamber containing units to be dispensed and a front face, the front face having a panel of instructions, a slot for the receipt of money, three buttons adapted to be depressed by a user following the insertion of money into the slot to indicate whether one or two or three units are to be dispensed, and an opening in the lower extent of the machine through which a user may reach to withdraw units from the machine following the insertion of money and depression of a button;

a plurality of units located within the chamber to be dispensed, each unit containing an analyzer and a sanitary wrapper therearound;

each analyzer formed as a generally rectilinear box with a first indicator on one face, a second indicator on a second face and an extendable tube on a third face, the extendible tube being reconfigurable between a reduced orientation adjacent to the third face when wrapped within the wrapper and an extended orientation for being gripped by the mouth of the user during the analyzing of the user's breath and with a slot in the third face adjacent to the tube;

the first indicator including an alcohol indicator comprising a rotatable indicator arrow and an indicating the percent of alcohol within the breath detected; of the user and the second indicator including a diaphragm through which the user's breath may flow to exterior of the device and an associated color gauge thereadjacent whereby the diaphragm will change colors as a function of the percent of alcohol in the breath of the user for being compared with the color on the gauge.

* * * * *